(12) United States Patent
Huh

(10) Patent No.: US 12,661,269 B2
(45) Date of Patent: Jun. 23, 2026

(54) WELDING INFORMATION PROVIDING APPARATUS

(71) Applicant: OTOS WING CO., LTD., Seoul (KR)

(72) Inventor: Sung Won Huh, Seoul (KR)

(73) Assignee: OTOS WING CO., LTD., Seoul (KR)

( * ) Notice: Subject to any disclaimer, the term of this patent is extended or adjusted under 35 U.S.C. 154(b) by 685 days.

(21) Appl. No.: 17/793,340

(22) PCT Filed: Jan. 4, 2021

(86) PCT No.: PCT/KR2021/000035
§ 371 (c)(1),
(2) Date: Jul. 15, 2022

(87) PCT Pub. No.: WO2021/149942
PCT Pub. Date: Jul. 29, 2021

(65) Prior Publication Data
US 2023/0053923 A1 Feb. 23, 2023

(30) Foreign Application Priority Data

Jan. 22, 2020 (KR) ......................... 10-2020-0008759

(51) Int. Cl.
*A61F 9/06* (2006.01)
*B23K 9/095* (2006.01)
(Continued)

(52) U.S. Cl.
CPC .............. *A61F 9/067* (2013.01); *A61F 9/064* (2013.01); *B23K 9/0956* (2013.01); *B23K 9/322* (2013.01);
(Continued)

(58) Field of Classification Search
CPC . A61F 9/067; A61F 9/064; A61F 9/06; B23K 9/0956; B23K 9/322; B23K 31/125;
(Continued)

(56) References Cited

U.S. PATENT DOCUMENTS

| 10,610,775 B1 * | 4/2020 | Ebert | ....................... G06F 3/013 |
| 2008/0158502 A1 * | 7/2008 | Becker | .................... A61F 9/067 |
| | | | 351/44 |

(Continued)

FOREIGN PATENT DOCUMENTS

| CN | 104698586 A | 6/2015 |
| KR | 10-2018-0113449 A | 10/2018 |

OTHER PUBLICATIONS

International Search Report for PCT/KR2021/000035 mailed Jun. 9, 2021, all pages.

(Continued)

*Primary Examiner* — William R Alexander
*Assistant Examiner* — Gabriel A Sanz
(74) *Attorney, Agent, or Firm* — Kilpatrick Townsend & Stockton LLP

(57) ABSTRACT

Provided is a welding information providing apparatus including a main body provided to be worn by a user, a display unit, which is arranged in the main body and includes a display for displaying a welding image to the user, a primary lens member, which is arranged on a path through which the welding image provided from the display travels, and includes a convex surface for adjusting a size of the welding image to allow the welding image to reach both eyes of the user, at least one camera, which is mounted on an outer side of the main body and is configured to obtain a welding image frame with respect to a welding operation, and a processor configured to control the display to display the welding image generated based on the welding image frame.

14 Claims, 13 Drawing Sheets

(51) Int. Cl.

| | | |
|---|---|---|
| *B23K 9/32* | (2006.01) | |
| *B23K 31/12* | (2006.01) | |
| *F16P 1/06* | (2006.01) | |
| *G02B 27/01* | (2006.01) | |

(52) U.S. Cl.

CPC .............. *B23K 31/125* (2013.01); *F16P 1/06* (2013.01); *G02B 27/0172* (2013.01)

(58) Field of Classification Search

CPC .................. F16P 1/06; G02B 27/0172; G02B 2027/0138; G02B 27/017

See application file for complete search history.

(56) References Cited

U.S. PATENT DOCUMENTS

| | | | |
|---|---|---|---|
| 2009/0235420 | A1 | 9/2009 | Chiang |
| 2012/0291172 | A1 | 11/2012 | Wills et al. |
| 2015/0103152 | A1* | 4/2015 | Qin .................... G02B 27/0176 |
| | | | 348/53 |
| 2016/0062120 | A1* | 3/2016 | Gupta .................... G02B 27/01 |
| | | | 359/630 |
| 2017/0258639 | A1 | 9/2017 | Wu |
| 2018/0071854 | A1* | 3/2018 | Matthews .............. H04N 7/183 |
| 2019/0129181 | A1* | 5/2019 | Polcak .............. G02B 27/0093 |
| 2019/0235623 | A1 | 8/2019 | Pollard et al. |
| 2019/0369353 | A1* | 12/2019 | Franklin ............ G02B 27/0176 |
| 2020/0265749 | A1* | 8/2020 | Becker ................. B23K 9/0953 |
| 2021/0141212 | A1* | 5/2021 | Jacoby .............. G02B 27/0172 |
| 2022/0031515 | A1* | 2/2022 | Becker ................... G02C 7/101 |

OTHER PUBLICATIONS

Office Action for Chinese Application No. 202180009605.5 mailed Mar. 28, 2025 (no translation provided).

* cited by examiner

WELDING INFORMATION PROVIDING APPARATUS

CROSS-REFERENCE TO RELATED APPLICATION

The present application is a U.S. national phase application under 35 U.S.C. 371 of International Application No. PCT/KR2021/000035, filed on Jan. 4, 2021, which claims the benefit of Korean Patent Application No. 10-2020-0008759 filed on Jan. 22, 2020 in the Korean Intellectual Property Office, the entire disclosure of each of which is incorporated herein by reference.

TECHNICAL FIELD

An embodiment of the present disclosure relates to a welding information providing apparatus.

BACKGROUND ART

Wearing a protector is to protect an operator from light, high temperature, or the like generated during a welding operation. The operator wearing the protector may visually confirm, through the protector, only whether welding is being performed, and thus has to inconveniently take off the protector to check, with the naked eye, various pieces of welding-related information, such as conditions set in a welding apparatus.

When the operator is not highly skilled and, in particular, is wearing an automatic welding helmet or a manual welding helmet, the operator is able to see only a region adjacent to welding light, and has difficulty in recognizing a detailed welding situation, such as an environment surrounding a welding site. Therefore, there is a need to provide the operator with a high-quality image for visually checking the environment surrounding the welding site, and provide the operator with detailed welding state information.

Furthermore, the illumination intensity/luminance of a welding light spot is significantly high during a welding operation, and thus a darkening filter is used to protect the eyes of the operator from the welding light spot and facilitate the welding operation, in which case other regions than the welding light spot may be completely invisible, thus the welding operation may become significantly difficult, and the accuracy of welding may rather deteriorate.

Such an issue not only happens in a welding operation, but may also affect medical staff performing skin procedures and/or treatments using high-luminance/illumination intensity light, such as laser light, and may also happen in other operations using high-luminance/illumination intensity light.

DESCRIPTION OF EMBODIMENTS

Technical Problem

The present disclosure has been made in view of the above-described necessity, and is to provide a welding information providing apparatus capable of showing an operator not only a welding spot but also an environment surrounding the welding spot, thereby improving the accuracy of welding by the operator.

However, this objective is merely illustrative, and the scope of the present disclosure is not limited thereto.

Solution to Problem

An embodiment of the present disclosure provides a welding information providing apparatus including a main body provided to be worn by a user, a display unit, which is arranged in the main body and includes a display for displaying a welding image to the user, a primary lens member, which is arranged on a path through which the welding image provided from the display travels, and includes a convex surface for adjusting a size of the welding image to allow the welding image to reach both eyes of the user, at least one camera, which is mounted on an outer side of the main body and is configured to obtain a welding image frame with respect to a welding operation, and a processor configured to control the display to display the welding image generated based on the welding image frame.

Advantageous Effects of Disclosure

A welding information providing apparatus according to embodiments of the present disclosure provides a user with a comfortable view through a primary lens member for providing both eyes of the user with a welding image provided from a display, and also stably provides a welding image even when the user is moving, for example, is turning his/her head. In addition, the welding information providing apparatus according to the embodiments of the present disclosure may provide an optimal welding image considering the individual visual acuity and amplitude of accommodation by moving the primary lens member forward and backward or adjusting the angle thereof.

BEST MODE

Figure 1:
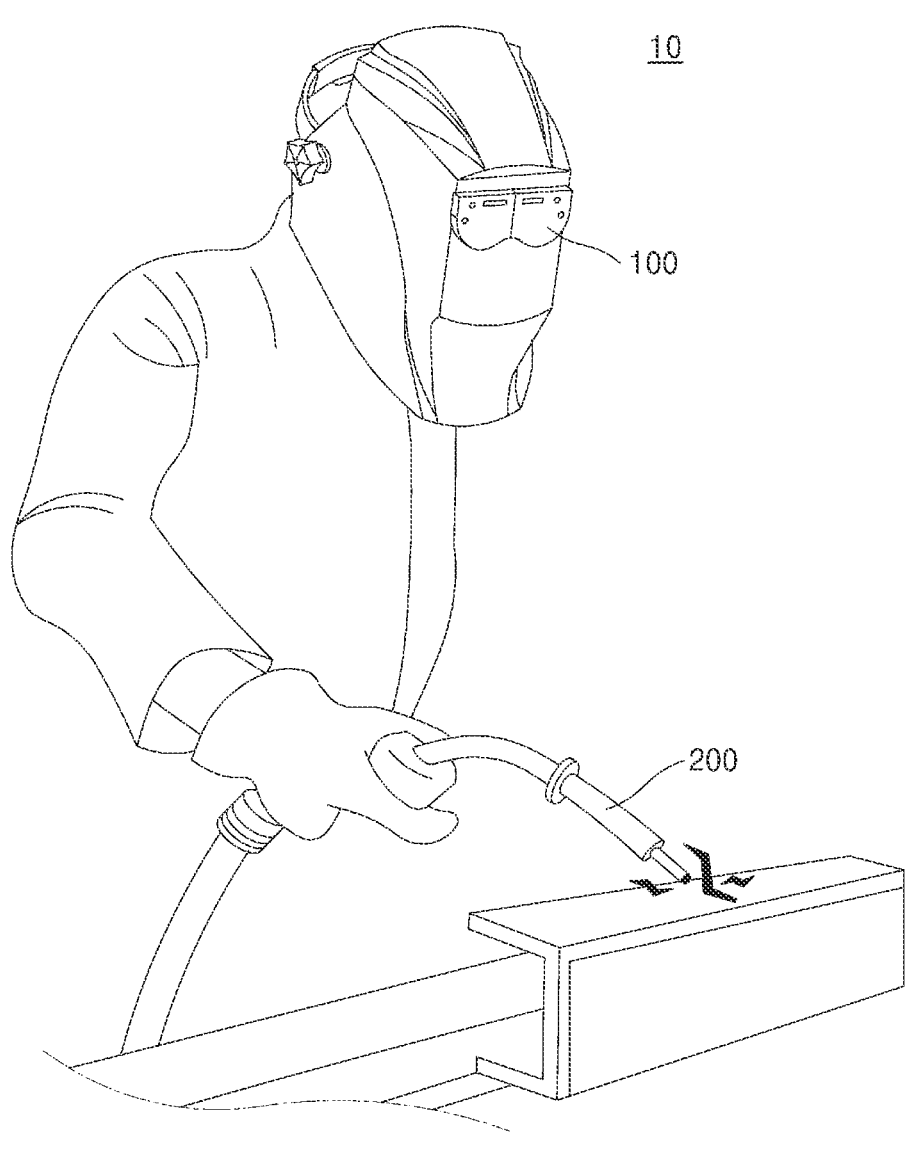
FIG. 1 is a diagram for describing a structure of a welding system according to an embodiment of the present disclosure.

An embodiment of the present disclosure provides a welding information providing apparatus including a main body provided to be worn by a user, a display unit, which is arranged in the main body and includes a display for displaying a welding image to the user, a primary lens member, which is arranged on a path through which the welding image provided from the display travels, and includes a convex surface for adjusting a size of the welding image to allow the welding image to reach both eyes of the user, at least one camera, which is mounted on an outer side of the main body and is configured to obtain a welding image frame with respect to a welding operation, and a processor configured to control the display to display the welding image generated based on the welding image frame.

According to an embodiment of the present disclosure, an imaginary center line passing through a center of the display unit may be between both eyes of the user.

According to an embodiment of the present disclosure, the imaginary center line may pass through the primary lens member.

According to an embodiment of the present disclosure, the primary lens member may include two convex surfaces corresponding to a left eye and a right eye of the user, respectively.

According to an embodiment of the present disclosure, when the primary lens member includes two convex surfaces, the primary lens member may include a left-eye lens corresponding to the left eye of the user and a right-eye lens corresponding to the right eye of the user, which are separable from each other.

According to an embodiment of the present disclosure, the primary lens member may be movable to adjust a distance between the primary lens member and the display.

According to an embodiment of the present disclosure, an angle of the primary lens member may be adjustable to cause one surface thereof facing the display to be inclined with respect to the display.

According to an embodiment of the present disclosure, the display unit may be movable to adjust a distance between the primary lens member and the display.

According to an embodiment of the present disclosure, an angle of the display unit may be adjustable to cause the display to be inclined with respect to the primary lens member.

According to an embodiment of the present disclosure, the welding information providing apparatus may further include a front body in which the display unit and the primary lens member are arranged, the front body maintaining a state in which the display unit and the primary lens member is spaced apart from each other.

According to an embodiment of the present disclosure, the front body may be installed in the main body to open and close one region of the main body.

According to an embodiment of the present disclosure, the welding information providing apparatus may further include a lens frame for fixing the primary lens member, and the lens frame may be installed in the front body to open and close one region of the front body.

Other aspects, features, and advantages other than those described above will be apparent from the following drawings, claims, and detailed description.

MODE OF DISCLOSURE

Hereinafter, embodiments will be described in detail with reference to the accompanying drawings, and the same or corresponding components will be denoted by the same reference numerals when described with reference to the accompanying drawings, and thus their descriptions that are already provided will be omitted.

As the present embodiments may be variously modified, particular embodiments will be illustrated in the drawings and described in detail in the detailed description. The effects and features of the present embodiments and methods of achieving them will become clear with reference to detail descriptions provided below with the drawings. However, the present embodiments are not limited to the descriptions below, and may be implemented in various forms.

As used herein, terms such as "first," "second," etc., are used only to distinguish one component from another, and such components must not be limited by these terms.

The singular expression used herein also includes the plural meaning as long as it is not inconsistent with the context.

The terms "comprises," "includes," "has", and the like used herein specify the presence of stated features or components, but do not preclude the presence or addition of one or more other features or components.

When a unit, region, or component is referred to as being "on" another unit, region, or component, it may be directly or indirectly on the other unit, region, or component, that is, one or more intervening units, regions, or components may be present therebetween.

When a component is referred to as being "connected to" or "coupled to" another component, the component may be directly connected to or in direct contact with the other component or intervening components may be present therebetween, unless clearly defined otherwise in the context.

It is to specify the presence of stated features or components, but not to preclude the presence or addition of one or more other features or components.

For ease of description, the magnitude of components in the drawings may be exaggerated or reduced. For example, each component in the drawings is illustrated to have an arbitrary size and thickness for ease of description, and thus the embodiments are not limited to the drawings.

FIG. 1 is a diagram for describing a structure of a welding system according to an embodiment of the present disclosure.

Referring to FIG. 1, a welding system 10 according to the present disclosure may include a welding information providing apparatus 100 and a welding torch 200. The welding information providing apparatus 100 and the welding torch 200 may be connected to each other through a communication network to transmit and receive data to or from each other. The welding information providing apparatus 100 and the welding torch 200 may be matched to each other in a one-to-one manner to operate, but are not limited thereto, and may be in a one-to-n relationship. That is, n welding torches 200 may be connected to one welding information providing apparatus 100, and one welding torch 200 may be connected to n welding information providing apparatuses 100. In addition, the welding information providing apparatus 100 and the welding torch 200 may communicate with a separate server (not shown) to transmit and receive data to or from each other.

The welding information providing apparatus 100 may provide an operator with information about a welding situation. In detail, the welding information providing apparatus 100 may obtain welding images by using at least one camera mounted on the welding information providing apparatus 100, generate a composite image based on the welding images, and display the composite image to the operator. In this case, the welding information providing apparatus 100 may generate the composite image by using high dynamic range (HDR) technology, and may display and provide a high-quality composite image to the operator. In this case, the operator may visually check the shape of a weld bead and information about an environment surrounding a region other than that adjacent to welding light, through the high-quality composite image.

In order to provide a high-quality composite image welding image, the welding information providing apparatus 100 according to an embodiment of the present disclosure may obtain images through two or more cameras and display each image through at least one display unit. In this case, the welding information providing apparatus 100 may repeatedly capture images while adjusting the shutter speed, ISO sensitivity, and gain value of each camera, and combine the images with each other. The welding information providing apparatus 100 according to an embodiment of the present disclosure may improve image quality through contrast processing on the obtained composite image.

In addition, the welding information providing apparatus 100 of the present disclosure may provide a function of displaying welding information in a preferred color (e.g., green and blue) by using RGB. Furthermore, the welding information providing apparatus 100 of the present disclosure may provide a function of adjusting the magnifying power of a magnifying glass (e.g., screen enlargement and reduction). In addition, the welding information providing apparatus 100 of the present disclosure may provide a temperature-combined image by using a separate thermal imaging camera. In this case, the welding information providing apparatus 100 may display a welding temperature in color. The welding information providing apparatus 100 of the present disclosure may support a function of providing a sound (e.g., a notification alarm) or a notification voice with respect to all of the above-described functions.

The welding torch 200 according to an embodiment of the present disclosure may detect, through at least one sensor, a welding situation including a welding temperature, a welding direction, a welding slope, a welding speed, and a distance between a base material and a welding torch with respect to a real-time welding operation. The welding torch 200 may monitor the state of the torch and may change a set value of a torch operation according to the welding situation.

The welding information providing apparatus 100 of the present disclosure may receive information about an operation setting and an operation state from the welding torch 200 through a communication network connected to the welding torch 200, and provide, through visual feedback, the operator with operation information based on received welding information.

For example, upon receiving sensing information about a welding temperature value, the welding information providing apparatus 100 may output a notification corresponding to the temperature value in various manners, such as light, a vibration, a message, or the like. In this case, the notification may be visual feedback provided to a display unit or a display of the welding information providing apparatus 100, or may be auditory feedback through a sound (e.g., a notification alarm) or a notification voice.

Meanwhile, the sensing information about a temperature value may include information about whether the temperature value is outside a preset temperature range, and the like. In addition, the sensing information about a temperature value may include a numerical value, a grade, a level, and the like corresponding to a temperature value of a welding surface.

The welding information providing apparatus 100 according to an embodiment of the present disclosure may induce the operator to stop the operation when it is determined that the temperature values of the torch and the welding surface are out of the preset temperature range. Welding with a temperature out of the preset temperature range, there is a risk of a deterioration in quality, and thus, the operator may be induced to adjust the temperature value of the torch.

When an abnormal current or voltage state of the welding torch 200 is detected, the welding information providing apparatus 100 according to an embodiment of the present disclosure may provide visual feedback for warning.

In this case, the visual feedback may be provided as an icon indicating danger, on a partial region of the display unit of the welding information providing apparatus 100 displaying an operation site. As another example, the welding information providing apparatus 100 may repeatedly increase and decrease the chroma of a particular color (e.g., red) on the entire screen of the display unit, to provide operation stop guiding through visual feedback.

According to an embodiment of the present disclosure, the welding information providing apparatus 100 may sense welding information through a sensor (e.g., a first sensor) included in the welding information providing apparatus 100, in addition to at least one sensor (e.g., a second sensor) included in the welding torch 200. In this case, the welding information may be sensed through at least one sensor, and the welding information may include a welding situation including a light intensity, a welding temperature, a welding direction, a welding slope, a welding speed, and a distance between a base material and a welding torch, which are related to a real-time welding operation.

Likewise, the welding information providing apparatus 100 may provide guiding corresponding to the welding information based on the welding information detected through a sensor (e.g., the first sensor) included in the welding information providing apparatus 100.

According to an embodiment of the present disclosure, after the operation stop guiding is provided, the welding information providing apparatus 100 may sense a predefined motion of the user or a predefined voice of the user, to change an operation of the welding torch.

In another embodiment, when communication with the welding torch 200 is not smooth, the welding information providing apparatus 100 may obtain the temperature values of the torch and the welding surface through self-provided image sensing. For example, the welding information providing apparatus 100 may obtain the temperature values of the torch and the welding surface based on image data obtained through the thermal imaging camera.

The above-described example only describes a case in which information received from the welding torch 200 is welding temperature information, and the welding information providing apparatus 100 may provide a variety of guiding with respect to various pieces of welding information.

Figure 2:
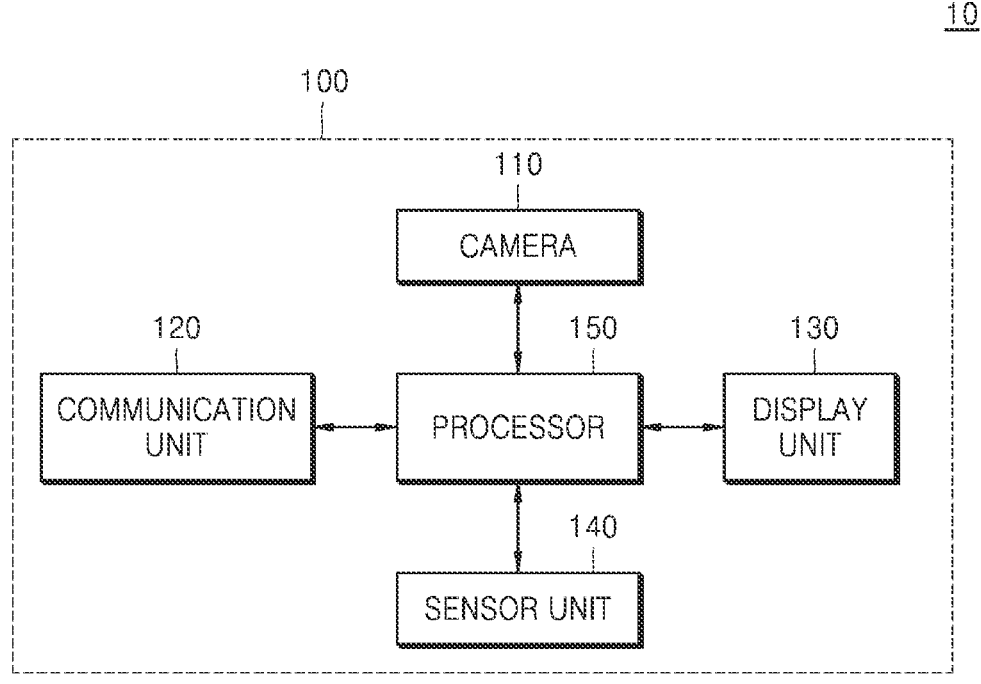
FIG. 2 is a schematic block diagram for describing components of a welding system according to an embodiment of the present disclosure.

FIG. 2 is a schematic block diagram for describing components of a welding system according to an embodiment of the present disclosure.

Referring to FIG. 2, the welding system 10 may include the welding information providing apparatus 100 and the welding torch 200. The welding information providing apparatus 100 may include a camera 110, a communication unit 120, a display unit 130, a processor 150, and a sensor unit 140.

The camera 110 may include at least one camera device, and may include a camera for capturing an image of a welding operation site. The camera 110 according to an embodiment of the present disclosure may be a camera located adjacent to the display unit 130 of the welding information providing apparatus 100. For example, a first camera and a second camera of the camera 110 may be mounted on one region of the front surface of the welding information providing apparatus 100 to be symmetrical with each other.

The camera 110 may receive a control command from the processor 150, change settings, such as the shutter speed, ISO sensitivity, and gain, in response to the control command, and then photograph the welding operation site. The camera 110 may include the first camera and the second camera, each of which may photograph the welding operation site by using different photographing settings.

The camera 110 according to an embodiment of the present disclosure may be included in one region of the front surface of the display unit 130, and may have a structure in which a light-shielding cartridge is located in front of a lens that receives light from an object.

An automatic light-shielding cartridge may block welding light generated when the operator performs a welding operation. That is, the automatic light-shielding cartridge (not shown) may increase its degree of light shielding by performing darkening based on welding light information sensed through the sensor unit 140, for example, a photo sensor. In this case, the automatic light-shielding cartridge may include, for example, a liquid-crystal display (LCD) panel, the degree of darkening of which may be adjusted according to the direction of alignment of liquid crystals. However, the present disclosure is not limited thereto, and the automatic light-shielding cartridge may be implemented with various panels, such as a vertical-alignment (VA) LCD, a twist nematic (TN) LCD, and an in-plane switching (IPS) LCD.

The degree of darkening of the automatic light-shielding cartridge may be automatically adjusted according to the brightness of the welding light. When the degree of darkening of the automatic light-shielding cartridge is automatically adjusted according to the brightness of the welding light as described above, the sensor unit 140 may be used. When the sensor unit 140 detects the intensity of the welding light to obtain welding light information and transmits, to the processor 150, information about the intensity of the welding light included in the welding light information by using a certain electrical signal, the processor 150 may control the degree of darkening based on the intensity of the welding light.

That is, the automatic light-shielding cartridge (not shown) may change the degree of light shielding of the panel in real time to correspond to the intensity of light generated on the welding surface in the welding operation site, and the camera 110 may capture a welding image in which a certain amount of welding light is shielded by the automatic light-shielding cartridge installed on the front surface thereof.

According to another embodiment of the present disclosure, the welding information providing apparatus 100 may not include the automatic light-shielding cartridge. In this case, the user may perform a welding operation only with a welding image obtained through the camera 110.

The camera 110 according to an embodiment of the present disclosure may include a thermal imaging camera. The welding information providing apparatus 100 may obtain a temperature image by combining a thermal image obtained through the thermal imaging camera with an image of the welding site.

According to an embodiment of the present disclosure, a lighting unit (not shown) electrically connected to the processor 150 may be further included. The lighting unit (not shown) is located outside the welding information providing apparatus 100 and is configured to emit light toward at least a welding operation area. The lighting unit (not shown) may include a plurality of light-emitting diode (LED) modules, and an output level of light emitted through the lighting unit (not shown) may be adjusted under the control by the processor 150. According to an embodiment, the lighting unit (not shown) may operate in conjunction with an operation of the camera 110 under the control by the processor 150.

The communication unit 120 is configured to receive welding information from the welding torch 200 and transmit a command for controlling the welding torch 200. According to an embodiment of the present disclosure, the communication unit 120 may transmit a composite image to an external device other than the welding torch 200. In this case, the external device may include various devices including a communication module, such as an operator/third-party smart phone or computer, etc.

The communication unit 120 may be configured to perform communication with various types of external devices according to various types of communication schemes. The communication unit 120 may include at least one of a Wi-Fi chip, a Bluetooth chip, a wireless communication chip, and a near-field communication (NFC) chip. In particular, when the Wi-Fi chip or Bluetooth chip is used, various pieces of connection information, such as a service set identifier (SSID) or a session key, may be first transmitted and received, and various pieces of information may be then transmitted and received after a communication connection is established by using the connection information. The wireless communication chip refers to a chip that performs communication according to various communication standards, such as Institute of Electrical and Electronics Engineers (IEEE), Zigbee, 3rd Generation (3G), 3rd Generation Partnership Project (3GPP), and Long-Term Evolution (LTE). The NFC chip refers to a chip that operates in an NFC scheme using a 13.56 MHz band among various radio frequency identification (RFID) frequency bands, such as 135 kHz, 13.56 MHz, 433 MHz, 860 MHz to 960 MHz, 2.45 GHz, or the like.

The display unit 130 is configured to provide a high-quality composite image to the operator. In detail, the display unit 130 may include a display 132 (see FIG. 4) for displaying, to the operator, a composite image obtained by combining images obtained through the camera 110 with each other.

According to an embodiment of the present disclosure, the rear surface of the display unit 130, i.e., a portion facing the user, may include the display 132 (see FIG. 4) for displaying a high-quality image to the user, and a primary lens member 135 (see FIG. 4) for allowing the user to view the display 132.

The display included in the display unit 130 may display a high-quality composite image such that the operator may visually check a surrounding environment other than a portion adjacent to the welding light (e.g., the shape of a previously welded bead). In addition, the display unit 130 may provide the operator with guiding on visual feedback (e.g., a welding progress direction) regarding a welding progress state.

The display 132 included in the display unit 130 may be implemented by using various display technologies, such as LCD, organic LED (OLED), LED, liquid crystal on silicon (LCoS), or digital light processing (DLP). In this case, the display according to an embodiment of the present disclosure may be implemented as a panel made of an opaque material, and the operator may not be directly exposed to harmful light. However, the present disclosure is not limited thereto, and the display may be provided as a transparent display.

The sensor unit 140 may include a plurality of sensor modules configured to detect various pieces of information about a welding site and obtain welding information. Here, the welding information may include a welding temperature, a welding direction, a welding slope, a welding speed, and a distance between a base material and a welding torch, which are related to a real-time welding operation. In addition, the sensor unit 140 may include an optical sensor module configured to detect a degree of light at least in a welding operation area.

According to an embodiment of the present disclosure, the sensor unit 140 may include an illuminance sensor, and in this case, the sensor unit 140 may obtain information about the intensity of welding light of a welding site. In addition to the illuminance sensor, the sensor unit 140 may further include various types of sensors, such as a proximity sensor, a noise sensor, a video sensor, an ultrasonic sensor, and a radio frequency (RF) sensor, and may detect various changes related to a welding operation environment.

The processor 150 may combine welding image frames received through the camera 110 with each other to generate a high-quality composite image. The processor 150 may set different photographing conditions of the camera 110 for respective frames and combine frames obtained in order of time with each other in parallel to obtain a composite image. In detail, the processor 150 may control the camera 110 to change the shutter speed, the ISO sensitivity, and the gain of the camera 110 and then capture an image.

In this case, the processor 150 may differently set the photographing condition according to sensed conditions such as welding light, ambient light, and a degree of movement of the welding torch 200 in the welding site. In detail, the processor 150 may set the photographing condition such that the ISO sensitivity and the gain decrease as the intensity of the welding light and/or the ambient light of the welding site increases. In addition, when it is detected that the movement and/or operation speed of the welding torch 200 is fast, the photographing condition may be set to increase the shutter speed.

The processor 150 may combine images of a preset number of frames with each other in parallel. According to an embodiment of the present disclosure, respective images in preset frames may be captured under different photographing conditions.

When two or more cameras 110 are provided, the processor 150 according to an embodiment of the present disclosure may control the cameras 110 to differently set their photographing setting conditions and then capture images. Also in this case, the processor 150 may combine images of a preset number of frames with each other in parallel.

The processor 150 may control the overall operation of the welding information providing apparatus 100 by using various programs stored in a memory (not shown). For example, the processor 150 may include a central processing unit (CPU), random-access memory (RAM), read-only memory (ROM), and a system bus. Here, the ROM is a component in which a command set for system booting is stored, and the CPU copies an operating system stored in the memory of the welding information providing apparatus 100 to the RAM according to a command stored in the ROM, and executes the operating system to boot a system. When the booting is completed, the CPU may copy various applications stored in the memory to the RAM, and execute the applications to perform various operations. Although it has been described above that the processor 150 includes only one CPU, the processor 150 may be implemented with a plurality of CPUs (or digital signal processors (DSPs), systems on a chip (SoC), etc.).

According to an embodiment of the present disclosure, the processor 150 may be implemented as a DSP, a microprocessor, and/or a time controller (TCON) for processing a digital signal. However, the present disclosure is not limited thereto, and the processor 150 may include one or more of a CPU, a microcontroller unit (MCU), a microprocessing unit (MPU), a controller, an application processor (AP), a communication processor (CP), or an Advanced RISC Machines (ARM) processor, or may be defined as the corresponding term. In addition, the processor 150 may be implemented as an (SoC) or large-scale integration (LSI) in which a processing algorithm is embedded, or may be implemented as a field-programmable gate array (FPGA).

Although not shown, the welding torch 200 may include a communication unit, a sensor unit, and a second processor.

The communication unit transmits and receives data to and from the welding information providing apparatus 100. The communication unit may include a module capable of performing short-range wireless communication (e.g., Bluetooth, Wi-Fi, Wi-Fi Direct) or long-range wireless communication (3G, High-Speed Downlink Packet Access (HSDPA) or LTE).

The sensor unit or the second sensor is included in the welding torch to sense a welding situation, such as a welding temperature, a welding speed, a welding slope, a welding direction, and a distance between a base material and the welding torch.

The sensor unit may detect at least one of various changes, such as a change in the posture of the user gripping the welding torch 200, a change in the illumination of a welding surface, a change in the acceleration of the welding torch 200, and the like, and transmit an electrical signal corresponding thereto to the second processor. That is, the sensor unit may detect a state change based on the welding torch, generate a corresponding detection signal, and transmit the generated detection signal to the second processor.

In the present disclosure, the sensor unit may include various sensors, and when the welding torch 200 is driven (or based on a user setting), power may be supplied to at least one preset sensor to sense a state change of the welding torch 200.

In this case, the sensor unit may include at least one of all types of sensing devices capable of detecting a state change of the welding torch 200. For example, the sensor unit may include at least one of various sensing devices, such as an acceleration sensor, a gyro sensor, an illuminance sensor, a proximity sensor, a pressure sensor, a noise sensor, a video sensor, a gravity sensor, and the like. Light intensity in a welding operation area detected through the illuminance sensor of the welding torch 200 may be transmitted to the processor 150 through the communication unit, and the processor 150 may control the lighting unit (not shown) and/or the camera 110 based on the light intensity transmitted through the illuminance sensor of the welding torch 200 without passing through the sensor unit 140 of the welding information providing apparatus 100.

Meanwhile, the acceleration sensor is a component for detecting a movement of the welding torch 200. In detail, the acceleration sensor may measure a dynamic force of the welding torch 200, such as acceleration, vibration, shock, or the like, and thus the movement of the welding torch 200 may be measured.

The gravity sensor is a component for detecting a direction of gravity. That is, a detection result of the gravity sensor may be used together with the acceleration sensor to determine the movement of the welding torch 200. In addition, a direction in which the welding torch 200 is gripped may be determined through the gravity sensor.

In addition to the above-described types of sensors, the welding torch 200 may further include various types of sensors, such as a gyroscope sensor, a geomagnetic sensor, an ultrasonic sensor, and an RF sensor, and may detect various changes related to a welding operation environment.

FIGS. 3A to 8 are diagrams schematically illustrating the welding information providing apparatus 100 according to an embodiment of the present disclosure.

Figure 3A:
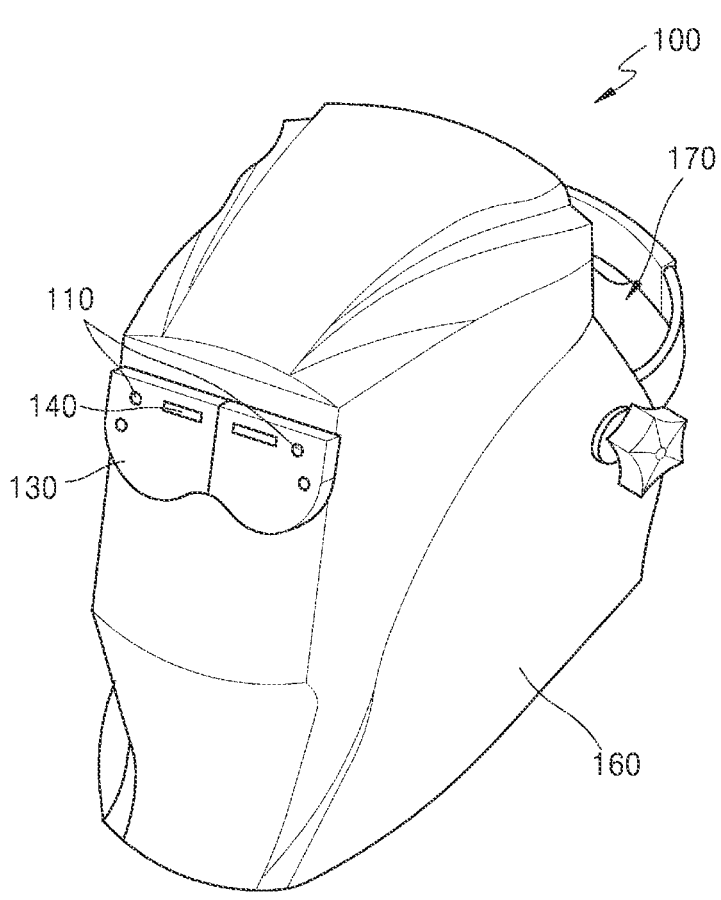
FIGS. 3A to 3C are perspective views illustrating welding information providing apparatuses each having a plurality of cameras according to different embodiments. FIG.
Figure 3B:
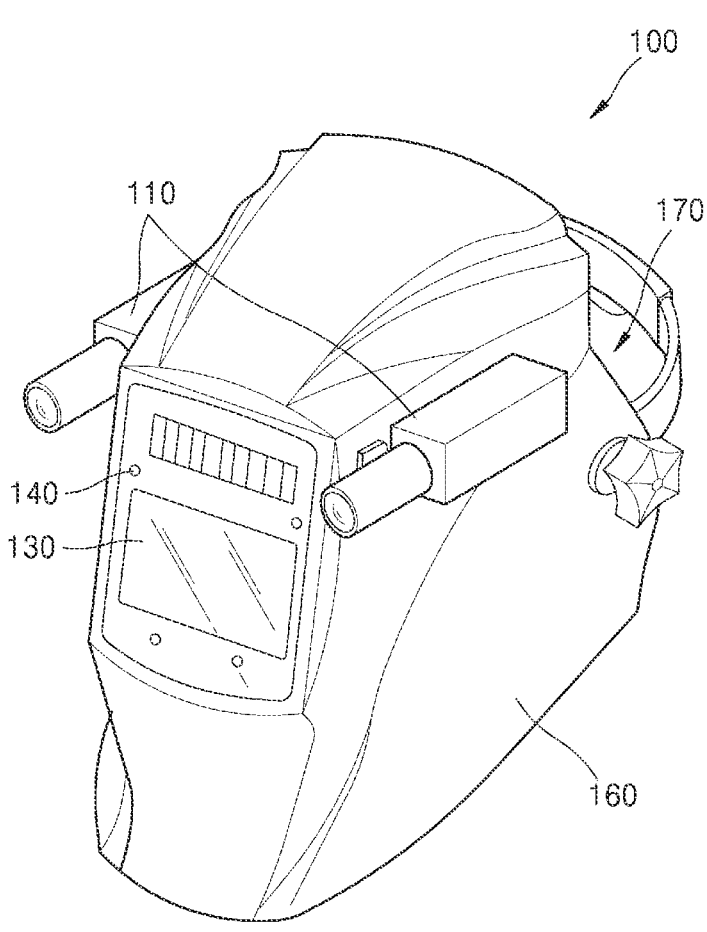
Figure 3C:
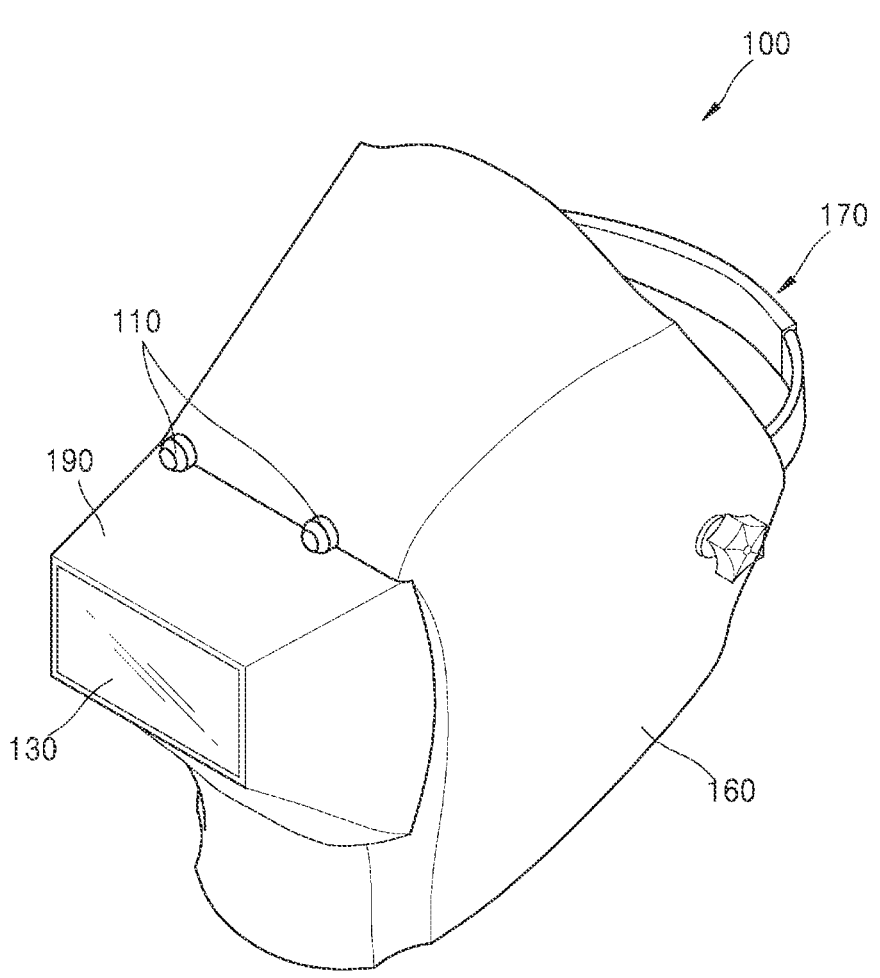

FIGS. 3A to 3C are perspective views illustrating welding information providing apparatuses each having a plurality of cameras according to different embodiments.

Referring to FIG. 3A, the welding information providing apparatus 100 of the present disclosure may include a main body 160, the display unit 130 installed on the front surface of the main body 160, at least one camera 110 mounted on one region of the front surface of the display unit 130, and the processor 150. In addition, the welding information providing apparatus 100 may include at least one sensor unit 140 and a fixing unit 170 arranged on the rear surface of the main body 160 to fix the welding information providing apparatus 100 to the head of the operator.

According to an embodiment, a plurality of cameras 110 may be provided. In particular, when two cameras 110 are provided, they may be symmetrically mounted on one region of the front surface of the display unit 130. In this case, the front surface of the display unit 130 may be an outer region (the region as illustrated in FIG. 3A) corresponding to the direction in which a welding operation is performed. On the contrary, the rear surface of the display unit 130 may be an inner region corresponding to the direction toward the face of the operator. However, the present disclosure is not limited thereto, and the camera 110 may be arranged in an outer region of the main body 160 corresponding to the direction in which the welding operation is performed.

Although FIG. 3A illustrates that the at least one sensor unit 140 (or a first sensor) is mounted on one region of the front surface of the display unit 130, according to an embodiment of the present disclosure, the sensor unit 140 may be included in the main body 160. In this case, the sensor unit 140 may be mounted in the direction toward the front of the main body 160 to detect a welding situation.

The main body 160 that protects the face of the operator may be formed of a material having a certain strength, for example, reinforced plastic, but the present disclosure is not limited thereto, and various materials may be used as long as the materials are resistant to elements that may occur during welding, such as sparks.

The fixing unit 170 is a component that directly contacts the head of the operator, and one side surface of the fixing unit 170, that is, at least a portion of the inner side surface that directly contacts the head of the operator may include a soft material, such as a fiber material or a cushion material.

Referring to FIG. 3B, the main body 160 of the present disclosure for protecting the face of the operator may include the display unit 130 and the sensor unit 140, which are installed on the front surface of the main body 160. In addition, the at least one camera 110 may be symmetrically mounted on both side surfaces of the main body 160. In addition, the welding information providing apparatus 100 may include the fixing unit 170 arranged on the rear surface of the main body 160 to fix the welding information providing apparatus 100 to the head of the operator.

In particular, two cameras 110 may be provided and may be mounted on both side surfaces of the main body 160 in a direction corresponding a direction of an operation performed by the operator. Although not shown in the drawing, when the number of cameras 110 is an odd number, the cameras 110 may be mounted on the central upper end of the main body 160.

In the present example, the rear surface of the display unit 130 faces the face of the operator, and the display 132 may be arranged on the rear surface of the display unit 130 to display a composite welding image to the operator. In addition, the front surface of the display unit 130 faces a region in which a welding operation is performed by the operator, and may display, when a predefined event occurs, a user interface (UI) showing a current state, such as a battery state of the welding information providing apparatus 100.

Although FIG. 3B illustrates that the at least one sensor unit 140 (or the first sensor) is mounted on one region of the front surface of the display unit 130, according to an embodiment of the present disclosure, the sensor unit 140 may be included in the main body 160. According to another embodiment, the sensor unit 140 may be included in at least a portion of the at least one camera 110 and then mounted.

Referring to FIG. 3C, the welding information providing apparatus 100 of the present disclosure may further include a front body 190 protruding outward from the main body 160. In the welding information providing apparatus 100 of the present disclosure, the display unit 130 may be arranged at a position spaced apart from eyes E of the user by a certain distance in order to secure the field of view of the user. To this end, in the welding information providing apparatus 100, the display unit 130 may be arranged on one side of the front body 190 protruding from the main body 160, such that the display unit 130 is spaced apart from the user. In this case, the at least one camera 110 may be mounted on a portion of the main body 160 adjacent to the front body 190.

Figure 4:
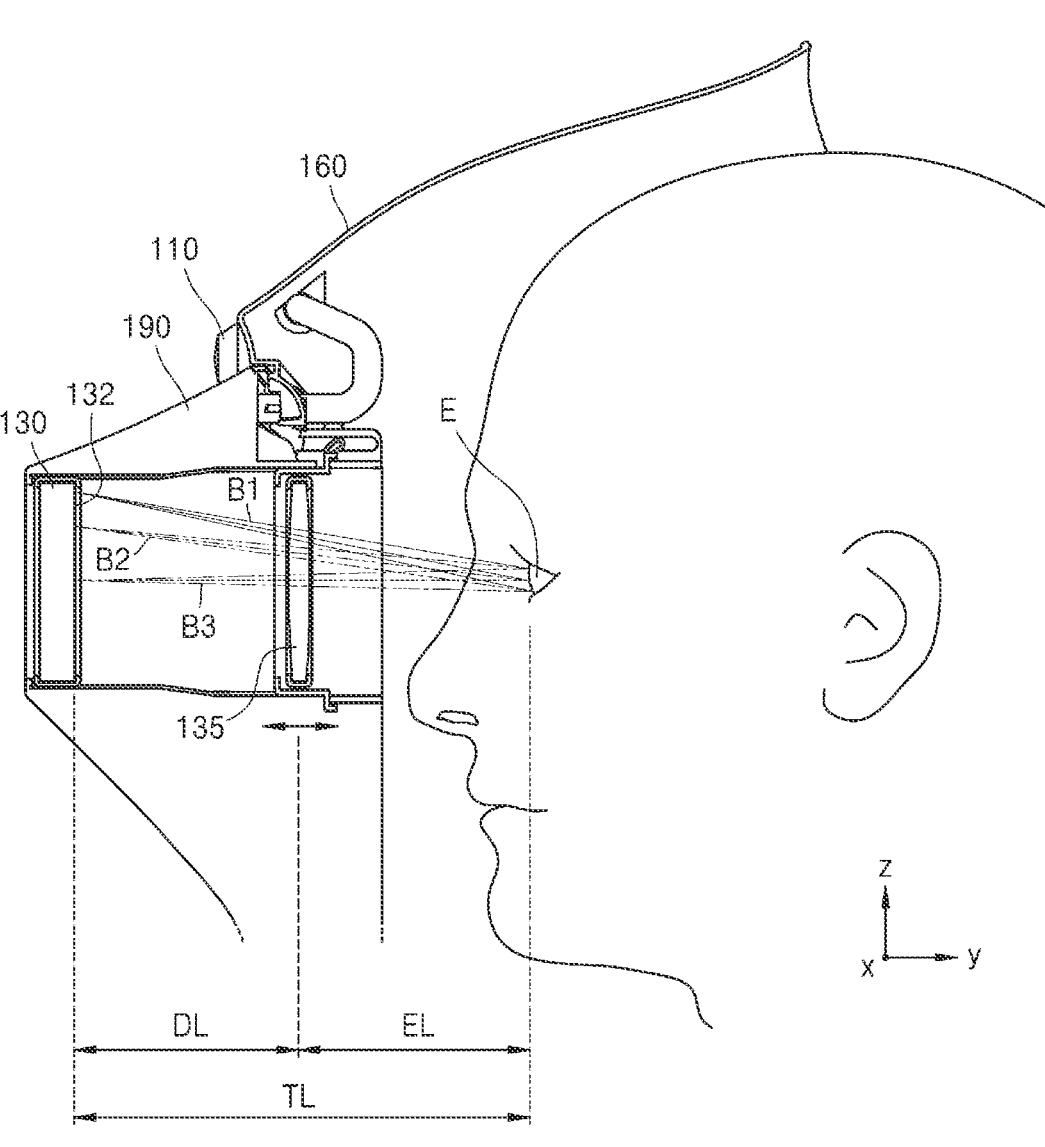
FIG. 4 is a side view for describing a welding information providing apparatus including a primary lens member according to an embodiment of the present disclosure.
Figure 5:
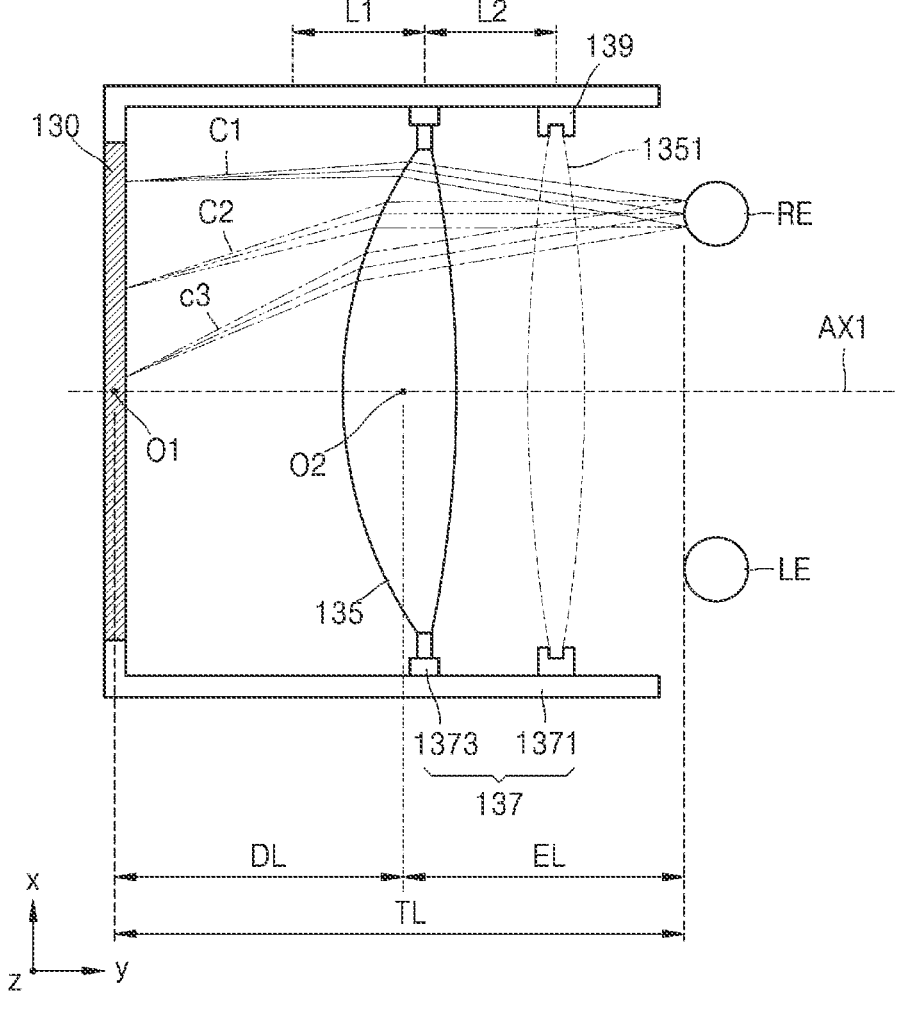
FIG. 5 is a plan view for describing a structure of a display unit and the primary lens member of FIG. 4.

FIG. 4 is a side view for describing a welding information providing apparatus including a primary lens member according to an embodiment of the present disclosure, and FIG. 5 is a plan view for describing a structure of a display unit and the primary lens member of FIG. 4.

Referring to FIGS. 4 and 5, the welding information providing apparatus 100 may include the primary lens member 135 for delivering, to both eyes of the user, a welding image provided from the display 132 at a short distance.

The welding information providing apparatus 100 according to an embodiment of the present disclosure provides a welding image through the display 132 spaced apart from the user by a certain distance in order to secure the field of view of the user. Accordingly, the user may be provided with the welding image from one display rather than through displays respectively corresponding to both eyes, and thus a wide field of view may be secured even in the enclosed space of the welding information providing apparatus 100. However, in this case, the welding information providing apparatus 100 may include the primary lens member 135 in order to provide the user with a welding image provided from the display 132 clearerly.

When one display 132 of the present disclosure is provided, an imaginary center line Ax1 passing through a center O1 of the display unit 130 may be between both eyes of the user. However, the present disclosure is not limited thereto, and a plurality of displays 132 may be arranged at positions spaced apart from both eyes of the user by certain distances.

The primary lens member 135 may be arranged on a path through which a welding image provided from the display 132 travels, and may include a convex surface to adjust the size of the welding image and guide the welding image to both eyes E of the user. The primary lens member 135 may be a convex lens including a convex surface to enlarge a provided welding image.

The primary lens member 135 may be formed of a glass material, a plastic material, or the like, and for the primary lens member 135 formed of a plastic material, a styrene resin such as a (meth)acrylic resin, a polycarbonate resin, an allyl resin, an allyl carbonate resin such as a diethylene glycol bisallyl carbonate resin (CR-39), a vinyl resin, a polyester resin, a polyether resin, a urethane resin obtained by reacting an isocyanate compound with a hydroxy compound such as diethylene glycol, a thiourethane resin obtained by reacting an isocyanate compound with a polythiol compound, a transparent resin obtained by curing a polymerizable composition containing a (thio)epoxy compound having at least one disulfide bond in a molecule, or the like may be used. In addition, the primary lens member 135 may be coated with a filter that blocks light of a particular wavelength band. For example, the primary lens member 135 may be a lens coated with a blue light blocking filter.

According to an embodiment, one surface of the primary lens member 135 facing the display 132 may be a convex surface. For example, the convex surface may have a curvature only in a first direction (y direction) toward the display 132, and may be flat without a curvature in a second direction (z direction) perpendicular to the first direction (y direction). Accordingly, the degree of refraction of the primary lens member 135 in the first direction (y direction) may be different from the degree of refraction in the second direction (z direction) perpendicular to the first direction (y direction). For example, the degree of refraction in the first direction (y direction) in which the curvature is formed may be greater than the degree of refraction in the second direction (z direction).

In detail, as illustrated in FIGS. 4 and 5, a welding image provided from the display 132 is provided to the eyes E of the user through the primary lens member 135. Here, light provided from positions B1, B2, and B3 different from each other with respect to the second direction (z direction), which is the vertical direction of the display 132, may be barely refracted and then provided to the eyes E of the user, whereas light provided from positions C1, C2, and C3 different from each other with respect to the first direction (x direction), which is the horizontal direction of the display 132, may be refracted and then provided to the eyes E of the user.

As illustrated, the primary lens member 135 may be formed as one lens covering a region corresponding to both eyes of the user, and in this case, the imaginary center line Ax1 passing through the center O1 of the display unit 130 may pass through the primary lens member 135. For example, the imaginary center line Ax1 may pass through the center O1 of the display unit 130 and a center O2 of the primary lens member 135. However, the primary lens member 135 of the present disclosure is not limited to only one lens, and may be formed by arranging two or more lenses with the same optical axis.

According to another embodiment, the primary lens member 135 may have two convex surfaces corresponding to a left eye LE and a right eye RE of the user, respectively. That is, the primary lens member 135 may be formed to have a structure in which a left-eye lens corresponding to the left eye LE and a right-eye lens corresponding to the right eye RE are connected to each other. The primary lens member 135 may be designed such that the diopter of a convex surface corresponding to the left eye LE and the diopter of a convex surface corresponding to the right eye RE are different from each other. In this case, the primary lens member 135 may focus a welding image provided from the display 132 through one lens member to be suitable for the visual acuity of the left eye LE and the right eye RE, and deliver the focused welding image to the user.

Meanwhile, the primary lens member 135 may be initially positioned at the halfway point of a total distance TL defined as the distance from the display 132 to the eyes E of the user. In other words, a distance DL between the display 132 and the initial position of the primary lens member 135 may be equal to a distance EL between the initial position of the primary lens member 135 and the eyes E of the user. Here, the total distance TL may be previously set by the structure of the front body 190 or the structure of the fixing unit 170, and the diopter of the primary lens member 135 may be determined by the total distance TL. However, the diopter of the primary lens member 135 is not simply determined by only the total distance TL, and may also be determined considering the diopter of the eyes of the user using the welding information providing apparatus 100.

For example, when the total distance TL is 12 cm, the required diopter of the lens is +8.0 diopters (D), users in their thirties or forties have an average amplitude of accommodation of +3.0 D, and thus the diopter of the primary lens member 135 may be determined to be +5.0 D. Here, the diopter of the eyes of the user is considered based on emmetropia in which parallel rays form an image on the retina without correcting the vision of the user, and when the user is wearing glasses, the amplitude of accommodation of the eyes of the user may have a different result value.

The primary lens member 135 may move forward and backward from its initial position. As described above, the diopter of the primary lens member 135 is determined considering the visual acuity of the user, but users have different visual acuity, and thus the welding information providing apparatus 100 of the present disclosure may adjust the distance between the primary lens member 135 and the user so as to provide a welding image with optimal image quality. To this end, the welding information providing apparatus 100 of the present disclosure may further include a distance adjusting member 137 for adjusting the distance between the primary lens member 135 and the display 132.

The distance adjusting member 137 may include a lens frame 1373 for fixing the primary lens member 135, and a guide rail 1371 for allowing the lens frame 1373 to move forward and backward in the first direction (y direction). The distance adjusting member 137 may have a finely-adjustable structure that allows the user to manually adjust the distance in one direction, for example, in an adjustment screw manner, and may further include a driving unit that generates a driving force for moving the primary lens member 135 and the frame 1373, to be able to automatically adjust the distance. When an input signal for distance adjustment is provided through an external input unit, the processor 150 may control the distance adjusting member 137 to move the primary lens member 135 forward and backward.

In this case, the primary lens member 135 may be moved forward and backward by the distance adjusting member 137 by a first distance based on the initial position, and here, a first distance L1 or L2 may correspond to a quarter of the total distance TL defined as the distance between the display 132 and both eyes RE and LE of the user. Because there are differences in visual acuity and amplitude of accommodation between users, the welding information providing apparatus 100 may adjust the distance EL between the primary lens member 135 and the eyes E of the user or the distance DL between the primary lens member 135 and the display 132 by using the distance adjusting member 137 to adjust the focus. However, that the primary lens member 135 is out of focus even after the primary lens member 135 is moved by a certain distance means that the diopter of the primary lens member 135 is insufficient for focusing, and thus the welding information providing apparatus 100 of the present disclosure may control the primary lens member 135 to move forward and backward by only the preset first distance.

According to another embodiment, an auxiliary lens member 1351 may be added to the welding information providing apparatus 100 for the case in which focusing is unachievable by merely adjusting the distance of the primary lens member 135. To this end, the welding information providing apparatus 100 may further include a coupling unit 139 into which the auxiliary lens member 1351 may be inserted. For example, the auxiliary lens member 1351 may include a convex lens capable of providing additional refractive power. However, the present disclosure is not limited thereto, and various lenses having necessary functions other than convex lenses may be provided, and two or more lenses may be added, according to the visual acuity and amplitude of accommodation of the user. In addition, the auxiliary lens member 1351 and the primary lens member 135 may be arranged on the same optical axis.

Figure 6:
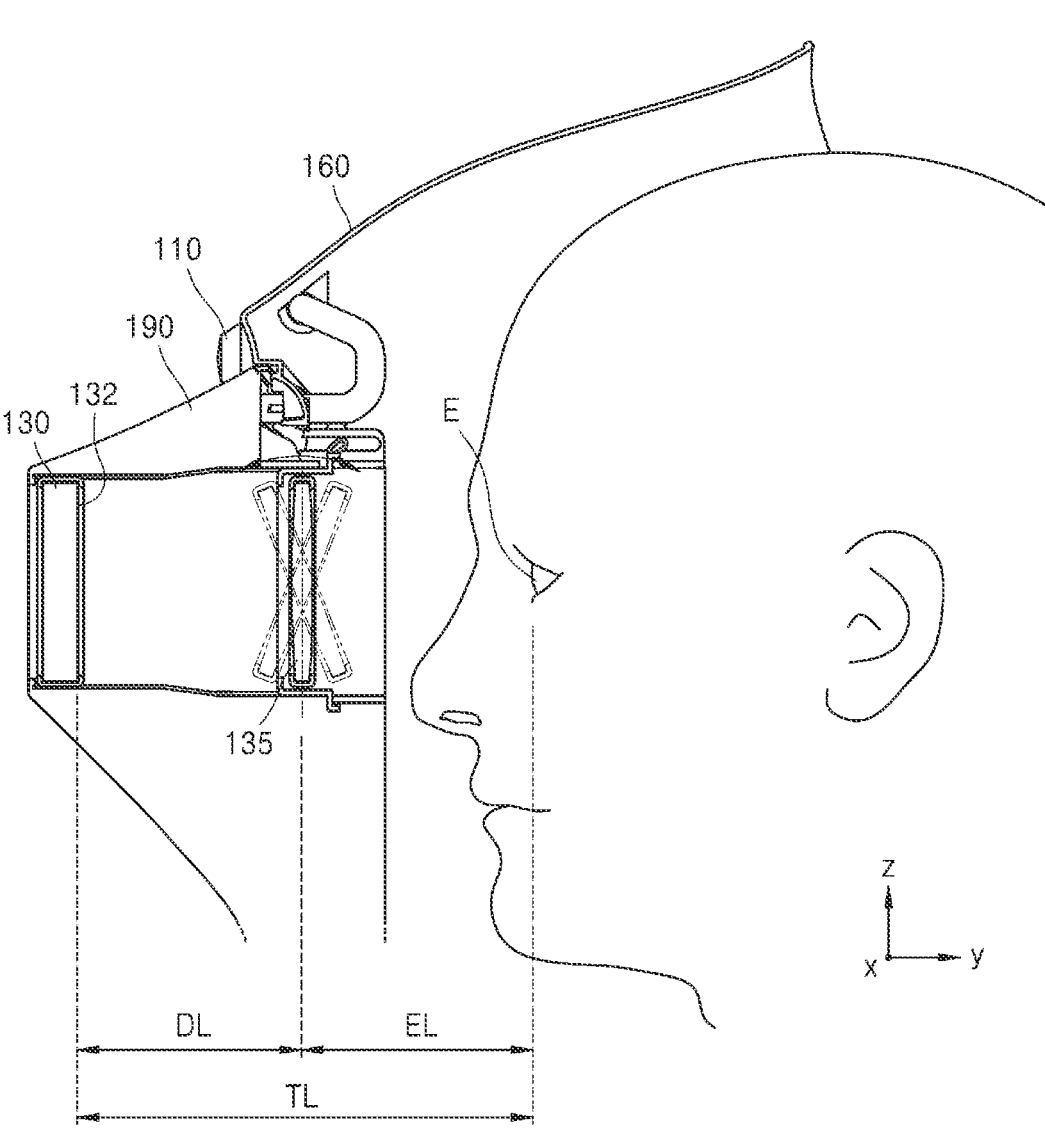
FIGS. 6 to 8 are diagrams for describing various embodiments of the present disclosure.
Figure 7:
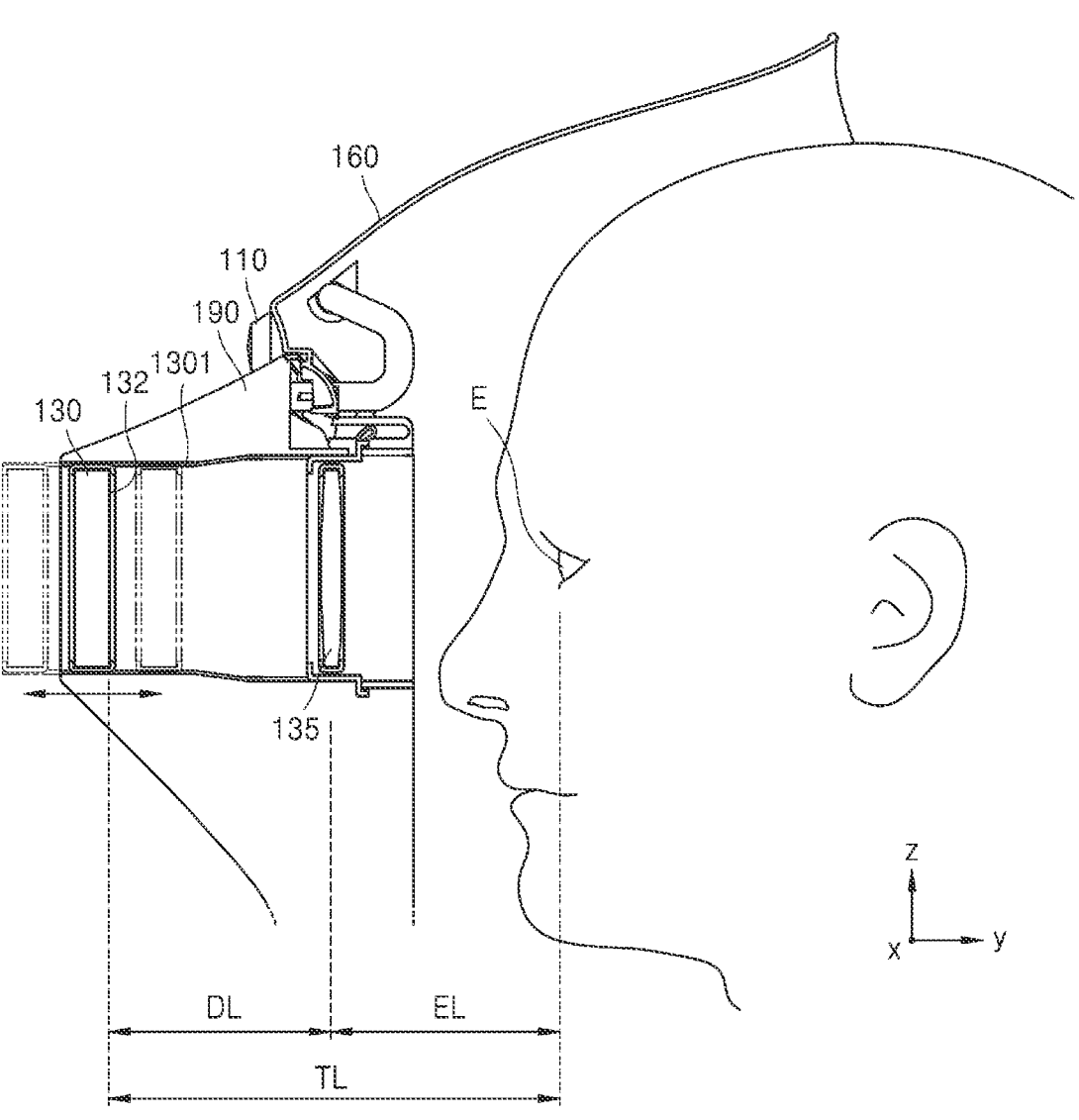
Figure 8:
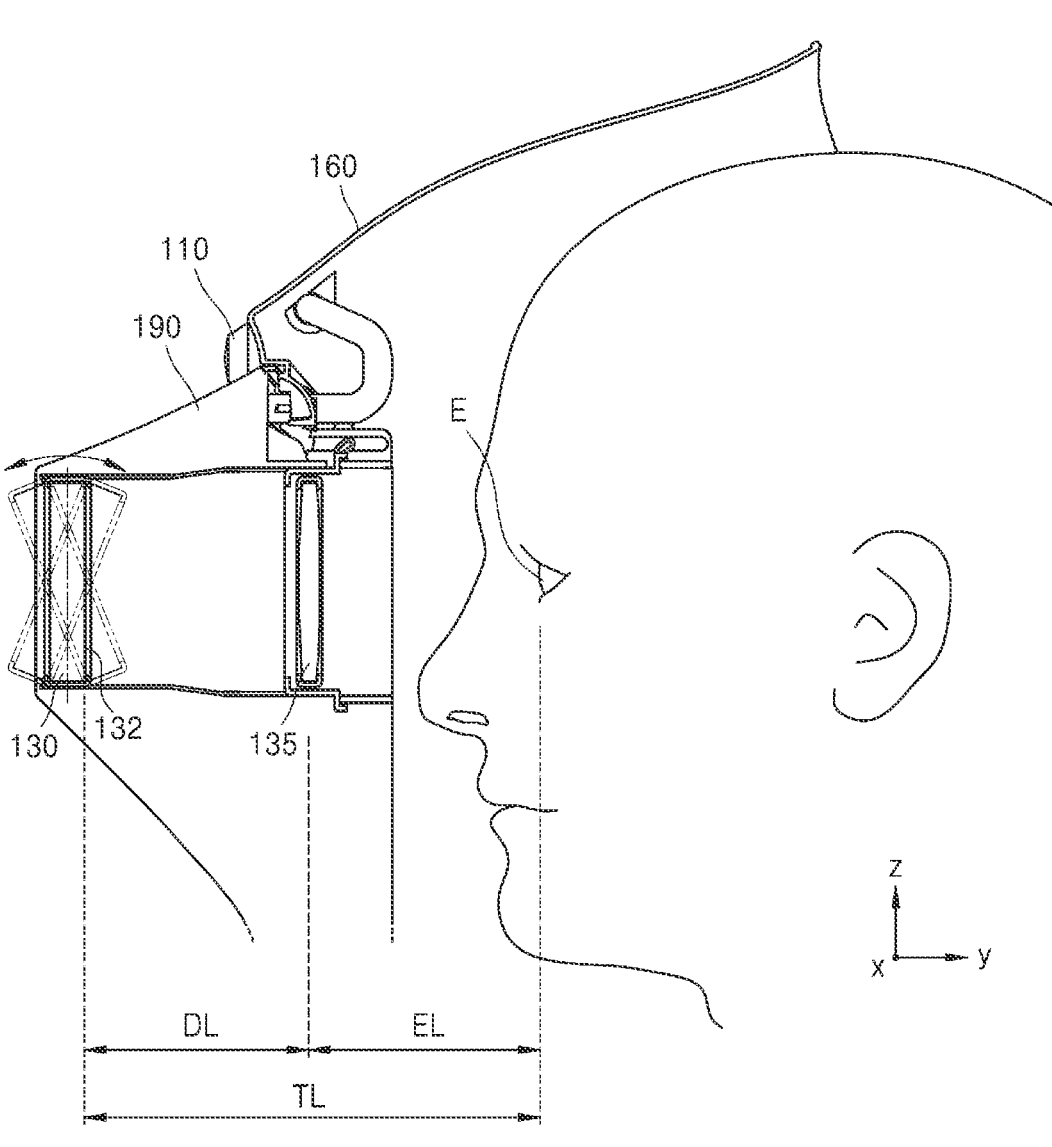

FIGS. 6 to 8 are diagrams for describing various embodiments of the present disclosure.

According to an alternative embodiment, referring to FIG. 6, the primary lens member 135 of the present disclosure may be provided to be tiltable forward or backward such that one surface thereof facing the display 132 is inclined with respect to the display 132. In other words, the primary lens member 135 may be configured to be rotatable about a rotation axis parallel to a third direction (x direction). For example, the frame 1373 for fixing the primary lens member 135 is rotatably connected to the guide rail 1371, and the user may adjust the angle of the primary lens member 135 by adjusting the frame 1373. Accordingly, the user may adjust the angle of the primary lens member 135 to be most suitable for the user under various conditions including the wearing state of the welding information providing apparatus 100.

Meanwhile, referring to FIGS. 7 and 8, in the welding information providing apparatus 100 according to another embodiment of the present disclosure, the distance or angle of the display unit 130 including the display 132 may be adjusted. In more detail, in the welding information providing apparatus 100 according to another embodiment of the present disclosure, the display unit 130 may be configured to be movable forward and backward in the first direction (y direction), and thus the distance between the display 132 and the eyes E of the user or the distance between the display 132 and the primary lens member 135 may be adjusted.

Like the primary lens member 135, the display unit 130 may include a separate distance adjusting member to adjust the distance from the primary lens member 135 or adjust the distance between the display 132 and the eyes E of the user. For example, the welding information providing apparatus 100 may further include a lens barrel support 1301 for fixing the display unit 130 to one side. The distance adjusting member may move the lens barrel support 1301 forward and backward by manual distance adjustment by the user or automatic distance adjustment. Accordingly, the display unit 130 may be inserted into the front body 190 or may protrude outward from the front body 190.

In addition, the display unit 130 may be provided to be tiltable such that the display 132 is inclined forward or backward with respect to the primary lens member 135, like the primary lens member 135. In other words, the display unit 130 may be configured to be rotatable about a rotation axis parallel to the third direction (x direction). For example, a frame for fixing the display unit 130 is rotatably connected to the lens barrel support 1301, and the user may adjust the angle of the display unit 130 by adjusting the frame. Accordingly, the user may adjust the distance or angle of the display unit 130 as well as the primary lens member 135 to be most suitable for the user under various conditions including the wearing state of the welding information providing apparatus 100.

Meanwhile, the display unit 130 may enlarge a welding image in a digital manner and provide the enlarged welding image through the display 132. The user may select to enlarge the welding image by using an input unit as necessary, and the processor 150 may control the display 132 to provide the enlarged image when an input signal is provided from the input unit.

Figure 9A:
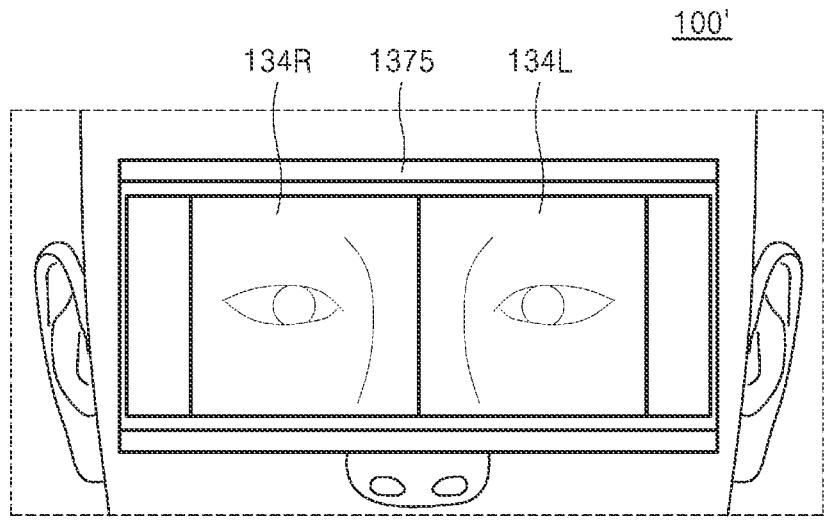
FIGS. 9A and 9B are diagrams illustrating only some components for schematically describing a welding information providing apparatus according to another embodiment.
Figure 9B:
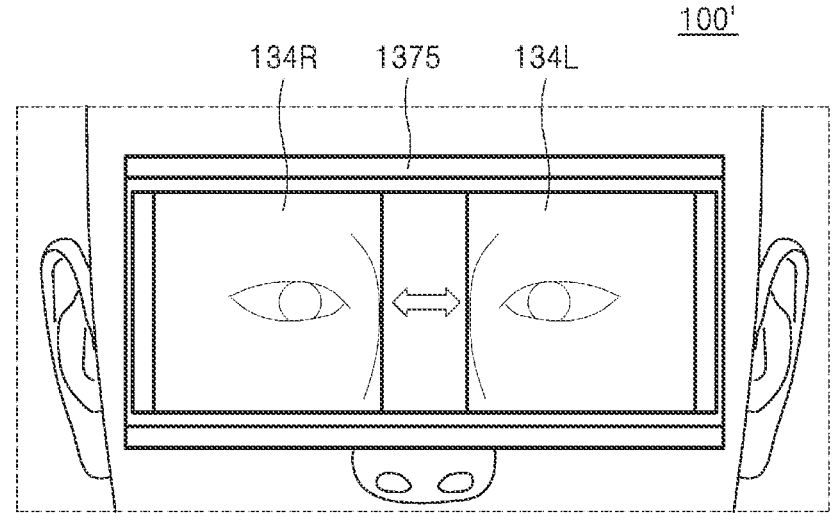

FIGS. 9A and 9B are diagrams illustrating only some components for schematically describing a welding information providing apparatus 100' according to another embodiment.

Referring to FIGS. 9A and 9B, the welding information providing apparatus 100' according to another embodiment may include two separate primary lens members 134R and 134L. In this case, the two separate primary lens members 134R and 134L may be movable in the horizontal direction (x direction), respectively. To this end, the welding information providing apparatus 100' may further include a guide frame 1375 for allowing the two separate primary lens members 134R and 134L to move in the horizontal direction (x direction). The two separate primary lens members 134R and 134L may be movably installed in the guide frame 1375 to independently move along the guide frame 1375. Through such a structure, the welding information providing apparatus 100' may provide a clearer welding image by applying lenses having different diopter corresponding to the visual acuity of the user whose both eyes have unequal visual acuity.

Figure 10:
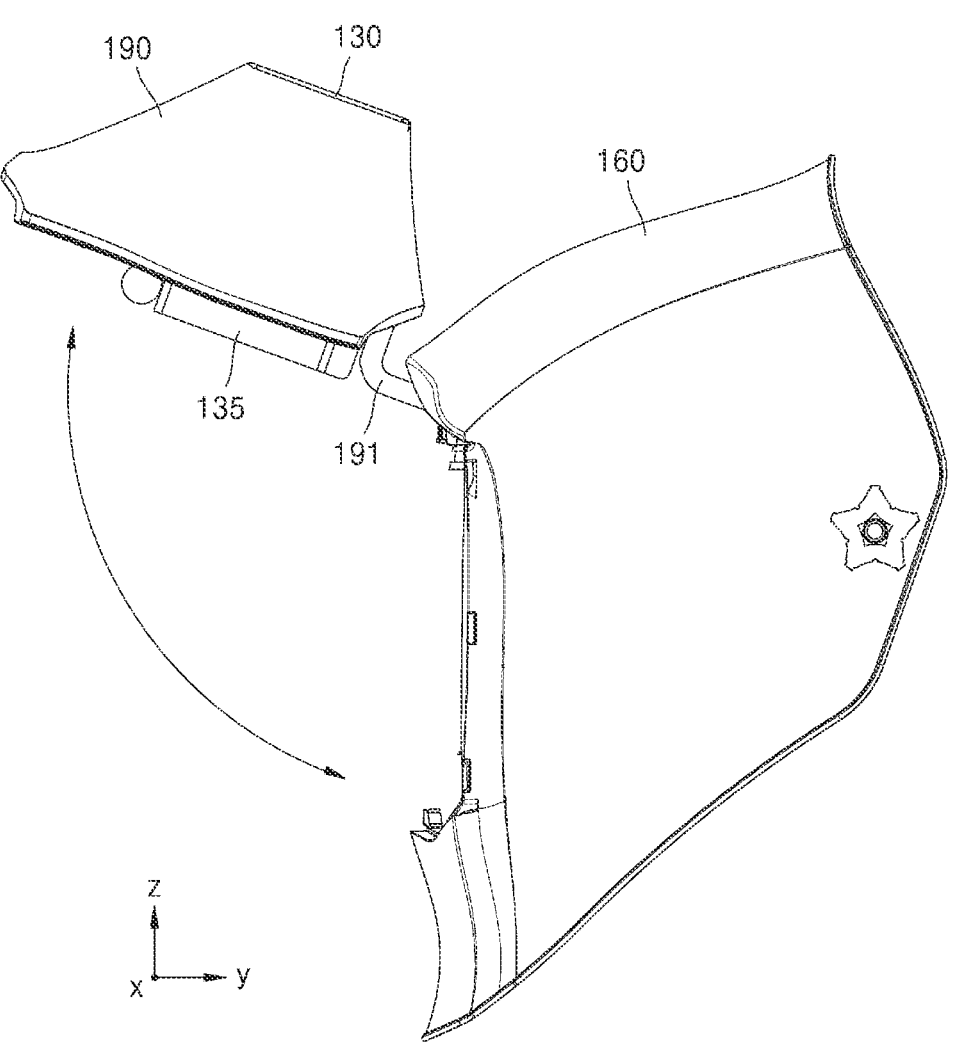
FIG. 10 is a diagram for describing a structure in which the front surface of a main body is opened by using a front body, according to the present disclosure.
Figure 11:
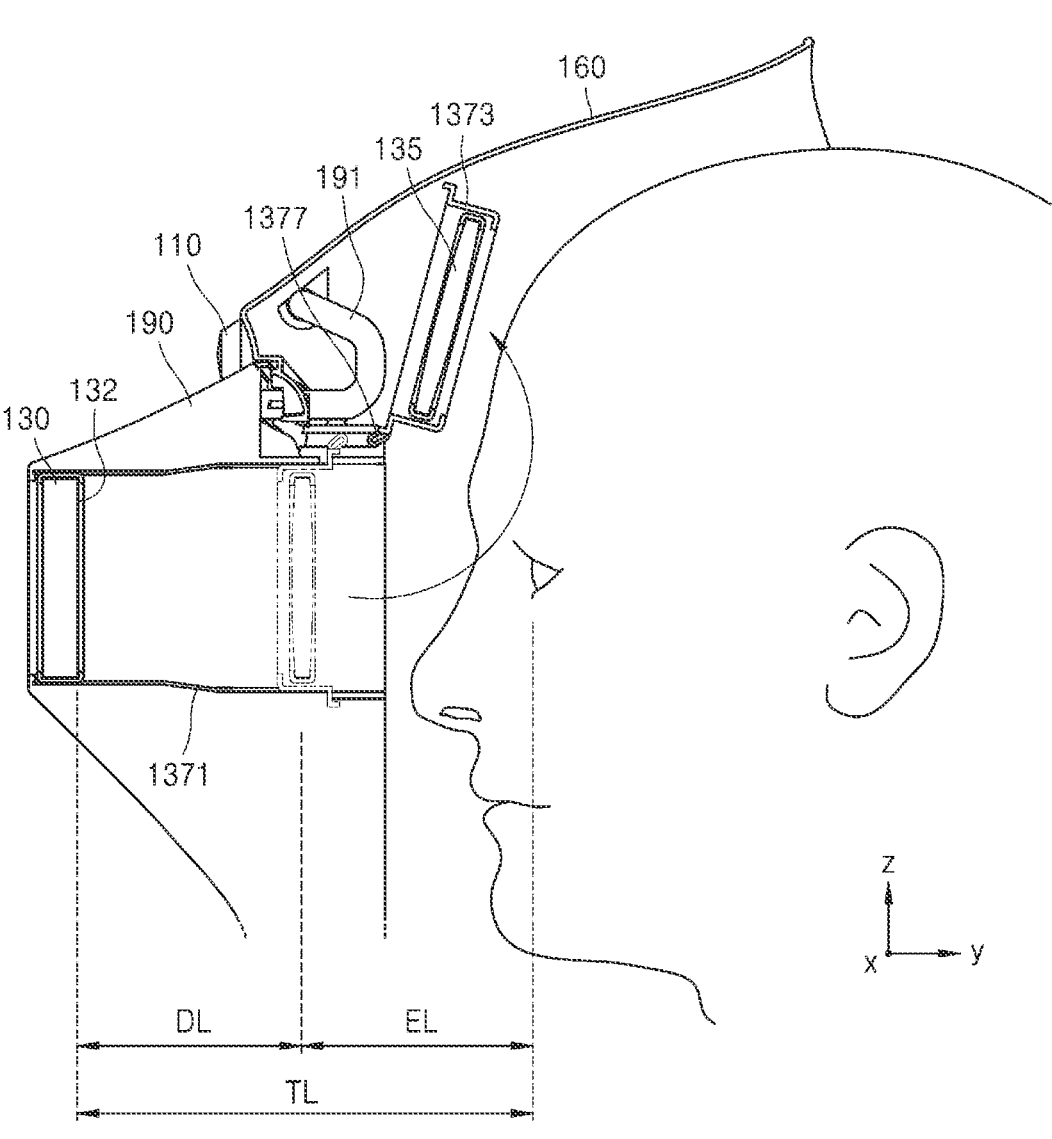
FIG. 11 is a diagram for describing a structure in which one region of a front body is opened by using a lens frame.

FIG. 10 is a diagram for describing a structure in which the front surface of a main body is opened by using a front body, according to the present disclosure, and FIG. 11 is a diagram for describing a structure in which one region of a front body is opened by using a lens frame.

Referring to FIG. 10, as described above, the front body 190 of the present disclosure may have the display unit 130 and the primary lens member 135 arranged therein, and may perform a function of maintaining a state in which the display unit 130 and the primary lens member 135 are spaced apart from each other. In other words, the front body 190 may protrude further than the main body 160 and the display unit 130 may be arranged at one side of the front body 190 such that a welding image is provided in a state in which the field of view of the user is secured. The welding information providing apparatus 100 includes the primary lens member 135 to provide the user with a clearer welding image, and the display unit 130 and the primary lens member 135 having the above-described structure may be arranged in the front body 190 to be spaced apart from each other as described above. In this case, the primary lens member 135 and the display unit 130 of the present disclosure may be installed to be movable forward and backward in the front body 190.

The front body 190 may be arranged to correspond to one region of the main body 160, and the one region of the main body 160 may be formed to be opened to expose the face of the user. The front body 190 may be installed in the main body 160 to open and close the one region of the main body 160. For example, the front body 190 may be hinge-coupled to one side of the main body 160 to open or close the one region of the main body 160 by rotating about a hinge shaft. Accordingly, the user may check a product of a welding operation with the naked eye or maximize ease of conversation with other operators.

Referring to FIG. 11, the primary lens member 135 of the present disclosure may be coupled to the front body 190 by the lens frame 1373. In this case, the lens frame 1373 may be coupled to the front body 190 to open and close one region of the front body 190. In detail, the lens frame 1373 for fixing the primary lens member 135 to the front body 190 may be hinge-coupled to one side of the front body 190 to open or close the one region of the front body 190 by rotating about a hinge shaft. In this case, the one region of the front body 190 corresponds to the display unit 130, and the display unit 130 may be directly exposed to the user by opening the primary lens member 135 and the lens frame 1373. Accordingly, when there is no need to view an enlarged welding image, the user may directly view a welding image provided from the display unit 130, and thus ease of use may be improved.

Meanwhile, the welding information providing apparatus 100 may include a connection structure 1377 that allows the lens frame 1373 for fixing the primary lens member 135 to move to the outermost side along the guide rail 1371 and then rotate at one end of the guide rail 1371. Accordingly, the welding information providing apparatus 100 may have a structure in which the primary lens member 135 may move forward and backward and one region of the front body 190 may be opened and closed.

As described above, the welding information providing apparatus according to embodiments of the present disclosure provides the user with a comfortable view through the primary lens member for providing both eyes of the user with a welding image provided from the display, and also stably provides a welding image even when the user is moving, for example, is turning his/her head. In addition, the welding information providing apparatus according to the embodiments of the present disclosure may provide an optimal welding image considering the individual visual acuity and amplitude of accommodation by moving the primary lens member forward and backward or adjusting the angle thereof.

Although the present disclosure has been described with reference to the embodiments illustrated in the drawings, they are merely exemplary, and it will be understood by one of skill in the art that various modifications and equivalent embodiments may be made therefrom. Therefore, the true technical protection scope of the present disclosure should be determined by the appended claims.

INDUSTRIAL APPLICABILITY

The present disclosure relates to a welding information providing apparatus, which is applicable to a protector for protecting an operator from light, high temperature, and the like generated during a welding operation.

The invention claimed is:

1. A welding information providing apparatus comprising:
a main body provided to be worn by a user;
a display unit arranged in the main body and including a display for displaying a welding image to the user;
a primary lens member arranged on a path through which the welding image provided from the display travels and including a convex surface for adjusting a size of the welding image to allow the welding image to reach both eyes of the user, wherein the primary lens member is rotatable about an axis located within the primary lens member and extending between a first end of the primary lens member and a second end of the primary lens member and wherein a surface of the primary lens member facing the display is adjustable in angle with respect to the display;
at least one camera mounted on an outer side of the main body and configured to obtain a welding image frame with respect to a welding operation;
a processor configured to control the display to display the welding image generated based on the welding image frame,
a front body protruding from the main body, in which the display unit and the primary lens member are arranged, wherein the front body is configured to maintain a state in which the display unit and the primary lens member are spaced apart from each other such that the display unit and the primary lens member are arranged along an imaginary center line passing through a center of the display unit, and
a lens frame coupled to the front body, wherein the lens frame is configured to support the primary lens member and rotate the primary lens member relative to the front body about the axis.

2. The welding information providing apparatus of claim 1, wherein
the imaginary center line is between both eyes of the user.

3. The welding information providing apparatus of claim 2, wherein
the imaginary center line passes through the primary lens member.

4. The welding information providing apparatus of claim 2, wherein
the primary lens member includes two convex surfaces corresponding to a left eye and a right eye of the user, respectively.

5. The welding information providing apparatus of claim 4, wherein,
when the primary lens member includes two convex surfaces, the primary lens member includes a left-eye lens corresponding to the left eye of the user and a right-eye lens corresponding to the right eye of the user, which are separable from each other.

6. The welding information providing apparatus of claim 1, wherein
the primary lens member is movable to adjust a distance between the primary lens member and the display.

7. The welding information providing apparatus of claim 1, wherein
the display unit is movable to adjust a distance between the primary lens member and the display.

8. The welding information providing apparatus of claim 1, wherein
an angle of the display unit is adjustable to cause the display to be inclined with respect to the primary lens member.

9. The welding information providing apparatus of claim 1, wherein
the front body is installed in the main body to open and close one region of the main body.

10. The welding information providing apparatus of claim 9, wherein the lens frame is installed in the front body to open and close one region of the front body.

11. The welding information providing apparatus of claim 1, wherein:

the path is defined from the display to an interior volume defined by the main body;

in a first state, the primary lens member is positioned along the path; and in a second state, the path is unobstructed by the primary lens member.

12. The welding information providing apparatus of claim 11, wherein the primary lens member is movable between the first state and the second state.

13. The welding information providing apparatus of claim 12, wherein the primary lens member is rotatable between the first state and the second state.

14. The welding information providing apparatus of claim 1, wherein the display unit is rotatable about an axis between a first end of the display unit and a second end of the display unit.

* * * * *